United States Patent [19]

Pollack et al.

[11] Patent Number: 5,057,598
[45] Date of Patent: Oct. 15, 1991

[54] MONOCLONAL ANTIBODIES REACTIVE WITH ENDOTOXIN CORE

[75] Inventors: Matthew Pollack, Bethesda; Kenneth W. Hunter, Kensington, both of Md.

[73] Assignee: Centocor, Inc., Malvern, Pa.

[21] Appl. No.: 304,884

[22] Filed: Feb. 1, 1989

Related U.S. Application Data

[63] Continuation of Ser. No. 771,178, Sep. 3, 1985, abandoned, which is a continuation of Ser. No. 492,374, May 6, 1983, abandoned.

[51] Int. Cl.$^5$ .................. A61K 39/395; C07K 15/28; C12N 12/05
[52] U.S. Cl. .................. 530/387; 530/388; 530/806; 530/808; 530/825; 435/70.21; 435/172.2; 435/172.3; 435/240.2; 435/240.26; 435/240.27; 424/85.8; 424/87
[58] Field of Search .............. 530/387, 395, 806, 808, 530/825; 424/87, 85.8, 92; 514/2, 8, 21; 435/240.2, 240.27, 172.2, 68

[56] References Cited

U.S. PATENT DOCUMENTS

| | | | |
|---|---|---|---|
| 4,172,124 | 4/1978 | Koprowski | 424/85 |
| 4,196,265 | 8/1978 | Koprowski | 424/85 |
| 4,237,224 | 1/1979 | Cohen et al. | 424/85 |
| 4,271,145 | 10/1979 | Wands et al. | 424/85 |
| 4,574,116 | 3/1986 | Kaplan | 435/240 |
| 4,594,325 | 6/1986 | Lundak | 435/240 |
| 4,677,070 | 6/1987 | Larrick | 435/240 |
| 4,683,196 | 7/1987 | McLaughlin | 435/7 |

OTHER PUBLICATIONS

Morse, S. A. et al., Journal of Infectious Diseases, 145(2):206–216 (2-1982).
Young, L. S. et al., Clinical Research, vol. 30, No. 2, p. 522A (1982).
Marks, M. I. et al., Journal of Clinical Investigation, 69:742–749 (4-1982).
Kirkland et al., J. Immunol., vol. 141, No. 9, p. 3208 (Nov. 1988).
Ziegler et al., N. Eng. J. Med., 324, pp. 429–436 (1991).
Bannerji et al., J. Imm., 123(6), 2558–62, (1979).
Ng et al., J. Gen. Micro., 94, 107–10, (1976).
Apicella et al., Inf. Imm., 34(3), 751–6, (1981).
Mattsby-Baltzer et al., J. Bacteriol., 159(3), 900–4 (1984).
Bruins et al., Inf. Imm., 21(3), 721–728, (1978).
Eskanazy et al., J. Clin. Microbiol., 16(2), 276–80 (8/1982).
Johns et al., Inf. Imm., 17(1), 9–15, (1977).
Kennett, "Cellfusion", Method Enzym, vol. 58, pp. 345–359, (1979).
Galanos et al., Eur. J. Bioch., 31, 230–3, (1972).

(List continued on next page.)

*Primary Examiner*—Esther L. Kepplinger
*Assistant Examiner*—Jeff Kushan
*Attorney, Agent, or Firm*—Hamilton, Brook, Smith & Reynolds

[57] ABSTRACT

Novel monoclonal antibodies are disclosed, the production of which is specified by particular genes contained, conveniently, in biologically pure cultures of self-reproducing carrier cells, such as, but not limited to, ATCC HB 8297 and ATCC HB 8298, such antibodies being reactive with at least part of endotoxin core of Gram-negative bacteria. Processes of preparing self-reproducing carrier cells, exemplified by ATCC HB 8297 and ATCC HB 8298, are disclosed. Also disclosed are processes of preparing the antibodies from the carrier cells which, conveniently, are cell lines such as hybridomas. Further disclosed are immunodiagnostic and immunodetection compositions and methods employing such antibodies. Still further disclosed are immunoprophylactic and immunotherapeutic compositions and methods utilizing the antibodies. Also disclosed are research compositions and methods employing the antibodies. And even further disclosed are compositions and methods utilizing the antibodies, useful for the purification or removal of endotoxin from solutions or mixtures which contain it.

17 Claims, 4 Drawing Sheets

OTHER PUBLICATIONS

Apicella et al., Inf. Imm., vol. 26(3), 870–4, (1979).
Braude, Adv. Int. Med., 26, 427–45, (1980).
Apicella, J. Inf. Dis., 140(1), 62–72, (1979).
Apicella et al., Inf. Imm. 50(1), 9–14, (1985).
Murphy et al., Inf. Imm., 50(1), 15–21, (1985).
Ziegler, et al., New England Journal of Medicine, 307:1225–1230 (1982).
Hiernaux, et al., *Proc. Natl. Acad. Sci. U.S.A.*, 79:1616–1620, 1982.
Tyoku, et al., *Biological Abstracts*, vol. 66, Abstract 14686, 1978.
Rietschel, E. Th., et al., Scandinavian Journal of Infectious Diseases, Supplement, 31:8–21, 1982.
Kohler, G. and Milstein, C., Nature, 256:495, 1975.
Westphal, O., et al., Z. Naturforschung, 7b:148, 1952.
Galanos, C., et al., European Journal of Biochemistry, 9:245, 1969.
Bradford, M. M., Analytical Biochemistry, 72:248, 1976.
Luderitz, O. et al., Bacteriological Reviews, 30:192, 1966.
Wilkinson, S. G., in Surface Carbohydrates of the Prokaryotic Cell, I. W. Sutherland, editor, Academic Press, N.Y., 1977, pp.97–171.
Tsai, C., Frasch, C. E., Analytical Biochemistry, 119:115, 1982.
Skidmore, B. J., et al., Journal of Experimental Medicine, 142:1488, 1975.
Kearney, J. F., et al., Journal of Immunology, 123:1548, 1979.
Gefter, M. L., et al., Somatic Cell Genetics, 3:231, 1977.
Cohen, S. N., et al., Proceedings of the National Academy of Sciences, U.S.A., 70:3240, 1973.
Ullrich, A., et al., Science, 196:1313, 1977.
Goeddel, D. V., et al., Proceeding of the National Academy of Sciences, U.S.A., 76:106, 1979.
Hitzeman, R. A., Nature, 293:717, 1981.
Hunter, K., et al., Lancet, 2:798, 1982.
Nowinski, R., et al., Science, 210:537, 1980.
Steinitz, M., et al., Nature, 269:420, 1977.
Nowinski, R. C., et al., Science, 219:637, 1983.
Sinkovics, J. G. and Dreesman, G. R., Reviews of Infectious Diseases, 5:9, 1983.

MONOCLONAL ANTIBODIES REACTIVE WITH ENDOTOXIN CORE

U.S. GOVERNMENT RIGHTS

The invention described herein may be manufactured, used and licensed by or for the U.S. Government for governmental purposes only without the payment to the inventors of any royalties thereon.

This application is a continuation of application Ser. No. 06/771,178, filed 9/3/86, now abandoned, which is a continuation of application Ser. No. 492,374, filed May 6, 1983, now abandoned.

BACKGROUND OF THE INVENTION

This invention is related to the production and use of novel monoclonal antibodies reactive with any part of endotoxin core of Gram-negative bacteria, and self-reproducing carrier cells containing genes which code for monoclonal antibodies reactive with endotoxin core. The invention is directed to the antibodies, to processes of preparing the antibodies, to diagnostic, prophylactic, and therapeutic methods and compositions employing the antibodies, and to investigational, pharmaceutical, and other methods and compositions employing the antibodies.

Gram-negative bacteria are a ubiquitous and diverse group of microorganisms that cause a number of serious and often life-threatening infections. Lipopolysaccharides are the principal biochemical constituents of the external covering or cell wall which characterizes all Gram-negative bacteria. These lipopolysaccharides, or endotoxins as they are called, play a major pathophysiologic and immunologic role in Gram-negative infections. Antibodies directed toward bacterial lipopolysaccharides constitute a critical host defense against these toxic substances and against the organisms which produce them.

In addition to their direct role in Gram-negative infections, endotoxins possess diverse and potent biological activities which, when coupled with the widespread presence of endotoxins in man's internal and external environments, endow them with great medical, scientific, and economic importance.

In general, bacterial lipopolysaccharides consist of a highly variable outer region composed of repeating oligosaccharide (sugar) units comprising the so-called "0-specific side-chain", and a relatively constant core region containing a limited number of sugars, often including the trisaccharide 2-keto-3-deoxyoctonate (KDO), and the biologically active lipid A moiety. Lipid A's derived from a number of distinct bacterial groups show a close structural relationship, and in most cases studied, lipid A consists of a $\beta$1,6-linked glucosamine disaccharide with ester- and/or amide-linked long chain fatty acids and with other possible substitutions. The core region, which is sometimes referred to as core glycolipid or endotoxin core, may be considered a lipopolysaccharide (or endotoxin) of Gram-negative bacteria that is lacking its 0-specific side-chain. In addition, the endotoxin core structure may itself be incomplete on the basis of missing core sugars and/or other substituents. Thus, endotoxin core is incomplete lipopolysaccharide, lacking part or all of the 0-specific side-chain, and, in some cases, also lacking core sugars and/or other substituents while usually retaining lipid A. (See E. Th. Rietsche et al., *Scandinavian Journal of Infectious Diseases,* Supplement 31:8–21, 1982, which is hereby incorporated by reference).

Significantly, most Gram-negative bacteria, representing diverse genera and species and including almost all which are pathogenic for man, share highly analogous, immunologically cross-reactive endotoxin core structures. For purposes of this specification, endotoxin core will be defined as that part of the lipopolysaccharide or endotoxin of Gram-negative bacteria comprised of complete or incomplete, substituted or unsubstituted lipid A covalently bound to substituted and/or unsubstituted core sugars, said lipid A characterized, for example, by a phosphorylated $\beta$1,6-linked glucosamine disaccharide with ester- and/or amide-linked long chain fatty acids, and said core sugars distinguished by their location in an interconnecting position between lipid A and the repeating oligosaccharide units of the 0-specific side chain in the intact lipopolysaccharide molecule.

Antibodies to 0-specific side chains in the variable outer region of lipopolysaccharides are species- and typespecific, with protective activity derived from their ability to promote the phagocytosis (engulfment) and killing of infecting organisms by host phagocytes (white blood cells). In contrast, antibodies directed toward the lipid A-containing inner core region are broadly cross-reactive among a wide variety of Gram-negative bacteria and are thought to act by neutralizing the biological activities of endotoxin.

Antibodies are produced by living cells called plasma cells which are specialized for that function. Plasma cells are derived from other cells called B lymphocytes which bear receptors on their cell membrane with the same antigen specificity as the antibodies synthesized and secreted by the plasma cells. Each immunocompetent B lymphocyte and its progeny (clone) bears receptors with unique specificity. Foreign substances (antigens) bind to receptors on B lymphocyte cell membranes and stimulate these specific B lymphocyte clones to proliferate, differentiate into plasma cells, and produce specific antibodies. In simplified terms, there are as many lymphocyte clones as there are specific antibodies, and as many specific antibodies as there are distinct antigens. Conversely, each specific antibody is produced by plasma cells derived from a single clone of immunocompetent lymphocytes, and an individual exposed to (i.e., immunized with) a specific antigen, produces specific antibody to that antigen through expansion of the appropriate lymphocyte clone.

Antibodies are characterized by exquisite specificity for the antigen toward which they are directed. In reality, most antigens contain more than one antigenic site, so that multiple antibodies may be directed at single antigens. In addition, different antibodies with varying affinities (strength of antigen binding) may be directed toward single antigenic sites. Since multiple antibodies directed toward the same antigen are derived from different lymphocyte clones, they are referred to as "polyclonal" antibodies. The normal antibody response to most antigens is polyclonal. At the same time, a single antibody may react with multiple antigens or antigenic sites which have common or analogous molecular structures; such an antibody is called a cross-reacting antibody.

It can thus be appreciated that the total antibody repertoire of an individual is enormous in respect to both size and breadth, and that natural exposure of an individual to an invading microorganism or immunization with a complex antigen will result in a polyclonal antibody response. The serum from such an individual will contain a complex admixture of pre-existing and new antibodies characterized by a multitude of specificities and affinities.

Traditionally, polyclonal antibodies have been prepared by immunizing an animal or man with the material (antigen) toward which antibodies are sought. If the goal of immunization is the prevention or treatment of a specific disease, intoxication or infection, an individual may be immunized directly with the appropriate antigen (active immunization), or administered pre-formed antibodies or immune serum prepared by prior immunization of another individual with the same antigen (passive immunization). Both types of immunization have major shortcomings. In the case of active immunization, there may be insufficient time to achieve an adequate antibody response to prevent or treat a particular infection or disease. In addition, it is sometimes impossible to accomplish active immunization because of ineffective vaccines, the inability of certain groups (e.g., immunosuppressed persons and infants) to respond to vaccination, or untoward reactions sometimes associated with active immunization. Passive immunization, on the other hand, lacks specificity and is associated with a significant risk of transmissible infections such as hepatitis or other adverse reactions. Antisera, or immunoglobulins prepared from antisera, contain not only the desired antibody, but literally thousands of other antibodies as well. In fact, the desired antibody usually represents only a small fraction of the total antibody present in such antisera. It may be difficult, therefore, to achieve adequate levels of this antibody through passive immunization using such antisera. This poses additional risks to the patient as the infusion of large volumes of antisera or immunoglobulin greatly increases the likelihood of serious adverse reactions and infusion-related infections.

The non-therapeutic uses of polyclonal antibodies, as for example in immunological research and various biotechnological applications, may also be seriously hampered by the variability of antibody responses to many antigens and the lack of specificity of antisera which contain a wide variety of antibodies.

Thus, the heterogeneity and diversity of naturally acquired or immunization-induced antibodies, and the unpredictability of antibody responses to antigenic stimuli, are factors which seriously limit the practical use of these polyclonal antibodies for clinical or scientific purposes.

While the foregoing discussion of the limitations of polyclonal antibodies has been stated in general terms, these same limitations apply to the therapeutic and non-therapeutic uses of polyclonal antibodies directed toward endotoxin core specifically.

In summary, Gram-negative bacteria are a widely prevalent group of microorganisms that commonly cause serious and often life-threatening infections. These bacteria all produce lipopolysaccharides or endotoxins which confer upon them important pathogenic and immunologic properties. Endotoxins have broad medical, scientific and economic significance on the basis of their varied biological properties that goes well beyond their role in Gram-negative infections. Endotoxins from a wide variety of sources share a common or highly analogous core structure. Antibodies to this core structure cross-react with lipopolysaccharides produced by many different Gram-negative bacteria. These cross-reactive antibodies neutralize the biological activities of endotoxin, and appear to provide protection against serious Gram-negative infections. The utilization of naturally acquired or immunization-induced polyclonal antibodies reactive with endotoxin core is limited by the low immunogenicity of endotoxin, the lack of specificity of polyclonal antiserum, and the adverse reactions associated with conventional active or passive immunization.

SUMMARY OF THE INVENTION

In contrast with multiple or polyclonal antibodies are single or "monoclonal" antibodies. These are antibodies derived from a single lymphocyte clone, which makes them absolutely specific and homogeneous. In 1975, Kohler and Milstein (*Nature*, 256:495, 1975, which is hereby incorporated by reference), first described how monoclonal antibodies directed to sheep red blood cells may be prepared by fusing a specific antibody-producing B lymphocyte with a tumor cell, resulting in an "immortal" self-reproducing hybrid clone (or "hybridoma") that can synthesize, in a test tube (in vitro) or an animal (in vivo), a single, monoclonal antibody. Such a hybridoma is, in effect, a self-reproducing cell "factory" which can produce a potentially limitless supply of an antibody with single, pre-defined specificity.

We undertook to prepare novel self-reproducing cell lines which synthesized monoclonal antibodies directed toward endotoxin core, since such antibodies, if, indeed, they could be produced, would satisfy a number of critical needs not fulfilled by existing polyclonal or monoclonal antibody technology. Like polyclonal antibodies to endotoxin core, such monoclonal antibodies would be broadly cross-reactive among a wide variety of pathogenic Gram-negative microorganisms, and would therefore have great potential utility in the prevention and treatment of diseases due to these bacteria. However, they would be more useful than polyclonal antibodies as immunoprophylactic, therapeutic, and diagnostic reagents because of their exquisite specificity. Likewise, this specificity would also render such monoclonal antibodies more useful for immunological and biochemical studies of endotoxin, for affinity purification of endotoxin, and for the neutralization and/or removal of endotoxin from pharmaceuticals and other reagents. Furthermore, unlike conventional polyclonal antibodies, monoclonal antibodies reactive with endotoxin core could be produced in a potentially limitless and homogeneous supply, thus avoiding the problems imposed by the low immunogenicity of endotoxin, the variability of polyclonal antibody responses, and the resulting limitations in achievable levels or supplies of anti-endotoxin antibodies available for clinical and other applications.

As demonstrated in the Description of the Preferred Embodiments, below, we have invented, inter alia, a means to stimulate B lymphocytes which produce antibodies directed to endotoxin core and to successfully fuse them with plasmacytoma (tumor) cells, creating hybridomas that synthesize monoclonal antibodies reactive with endotoxin core. This invention thus provides a means to overcome, for the first time, the shortcomings of existing antibody technology outlined above.

It is accordingly one object of the present invention to provide self-reproducing carrier cells, such as exemplified by ATCC HB 8297 and ATCC HB 8298, containing genes that code for the production of monoclonal antibodies reactive with endotoxin core.

It is a further object to provide the antibodies so produced.

A still further object is to provide an in vitro process for producing the antibodies.

An even further object is to provide an in vivo process for mass-producing the antibodies from the carrier cells.

Another object is to provide methods and compositions for using the antibodies in the diagnosis, prophylaxis and treatment of disease caused by endotoxin-bearing pathogens.

Still another object is to provide research compositions containing the antibodies useful for immunological or biochemical analyses of endotoxins.

An even further object is to provide compositions containing the antibodies suitable for isolating or purifying endotoxin from mixtures containing endotoxin and other substances.

Another object is to provide compositions containing the antibodies useful for the neutralization and/or removal of endotoxin from other materials or solutions.

Other objects and advantages of the present invention will be set forth in part in the description which follows, and in part will be obvious from the description, or may be learned by practice of the invention.

In satisfaction of the foregoing objects and objectives there is provided by this invention monoclonal antibodies reactive with endotoxin core. The antibodies are produced by self-reproducing carrier cells containing genes that code for monoclonal antibodies reactive with endotoxin core. Also provided by the invention are carrier cells, which conveniently are cell lines such as hybridomas.

Additionally, there are provided in satisfaction of the foregoing objects and objectives in vitro processes that include culturing the carrier cells in a suitable medium for an appropriate period of time, and recovering the antibodies from the medium in which the carrier cells are grown. In addition, there is provided an in vivo process for mass-producing the antibodies. This process includes intraperitoneally administering to a histocompatible or immunosuppressed animal, carrier cells in an amount sufficient to initiate an ascites tumor, and recovering the antibodies from the ascites fluid of the animal after a period of time sufficient for the antibodies to be produced in a recoverable quantity.

Also provided by this invention is a method for the immunological detection of endotoxin, or for the diagnosis, in a human or an animal, of an infection caused by pathogenic microorganisms bearing endotoxin. This method includes mixing a diagnostically effective amount of the antibodies of this invention with a sample of endotoxin-containing solution such as a body fluid or tissue removed from the man or animal and measuring the degree of the reaction in the resulting mixture. The present invention also provides compositions for the detection of endotoxin or for the diagnosis of an infection caused by an endotoxin-bearing microorganism. These compositions include, in admixture with a diagnostically acceptable carrier, a concentration of the antibodies effective to detect endotoxin or to diagnose the infection.

Also provided by the present invention in satisfaction of the foregoing objects and objectives are immunologic methods for the passive prophylaxis or therapy of an infection, or its clinical manifestations or consequences, including septic shock, in a man or an animal, caused by an endotoxin-bearing microorganism. This method comprises the administration to said man or animal, prior to or during an infection caused by said microorganism a sufficient amount of the antibodies of this invention to result in the prevention or amelioration of the infection, or its clinical manifestations or consequences, including septic shock. Also provided are compositions for passive prophylaxis or therapy of such an infection, the compositions including, in admixture with a physiologically acceptable carrier, a concentration of the antibodies of this invention effective to result in passive prophylaxis or treatment.

There is also provided by this invention research compositions useful for carrying out immunological and biochemical analyses of endotoxins. These compositions include, in admixture with a carrier suitable for research, an amount of the antibody effective to provide such information when it is mixed with endotoxins.

There are further provided by this invention compositions useful for the isolation and purification of endotoxins from mixtures or solutions which contain them, the compositions including a suitable matrix for support of the antibodies effective in permitting isolation and purification of endotoxins by immune absorption.

There is still further provided by this invention compositions useful for the neutralization and/or removal of endotoxins from materials or solutions which contain them, such compositions including a suitable carrier or matrix to permit precipitation or immune absorption of these endotoxins from such materials or solutions which contain them.

The accompanying drawings and tables, which are incorporated in and constitute a part of this specification, illustrate and together with the description serve to explain the principle of the invention.

DESCRIPTION OF THE PREFERRED EMBODIMENTS

Figure 1:
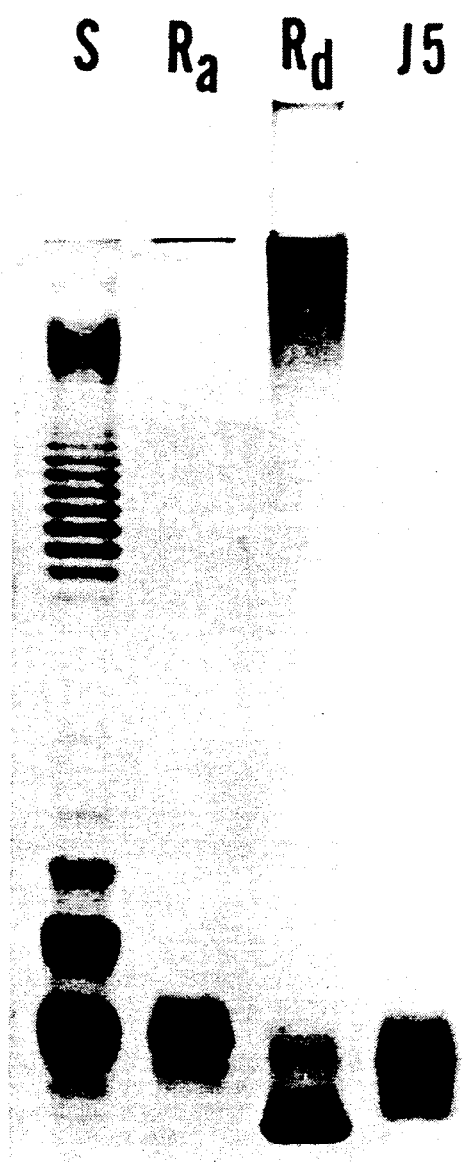
FIG. 1 depicts an analysis of purified endotoxin core by electrophoresis on 14% SDS polyacrylamide gel.

The preparation and characterization of self-reproducing carrier cells and resulting antibodies reactive with endotoxin core as well as various methods and compositions employing the antibodies, will be better understood by reference to the following description, which sets forth the preferred embodiments of the invention.

Two of the carrier cell lines embraced by this invention, by means of example only, are ATCC HB 8297 and ATCC HB 8298 which are biologically pure cultures available from the permanent collection of the American Type Culture Collection, 12301 Parklawn Drive, Rockville, Md., U.S.A. 20852.

As indicated, the scope of the present invention embraces any self-reproducing carrier cells, including, but not limited to, ATCC HB 8297 and ATCC HB 8298 containing genes that code for the production of monoclonal antibodies reactive with any part of endotoxin core of Gram-negative bacteria. This specification describes in detail the steps taken by the inventors to produce the above ATCC HB 8297 and ATCC HB 8298.

To make hybridomas (fused cells) that secrete monoclonal antibodies reactive with endotoxin core, in accordance with the invention, the following procedures were used.

The double, rough mutant derived from an *E. coli* 0111:B4 parent strain and designated "J5" (ATCC 39355, available from the American Type Culture Collection, 12301 Parklawn Drive, Rockville, Md., U.S.A. 20852) lacks the enzyme UDP-galactose 4-epimerase and is unable to incorporate exogenous galactose into its lipopolysaccharide structure. As a consequence of this mutation, the endotoxin produced by this strain lacks 0-specific side chains and outer core sugars, and consists only of lipid A and sugars present in the inner core (in this case comprising 2-keto-3-deoxyoctonate, heptose, glucose, and N-acetylglucosamine). The J5 strain was used in this case by way of example only. For the purposes of the invention, any bacterial strains bearing an endotoxin similar to that of the J5 strain could be used as a source of endotoxin core. So-called "rough" mutants are the preferred organisms for this purpose since their endotoxin, like that of the J5 strain, lacks 0-specific side chains and at least part of the outer core structure, thus exposing immunodeterminants associated with the cross-reacting inner core. Alternatively, endotoxin might be obtained from so-called "smooth" organisms whose lipopolysaccharide structure is relatively complete. The endotoxin from such strains could be physically or chemically degraded to yield a core structure analogous to that obtained from rough mutant strains, such as the J5 mutant, useful in the production of monoclonal antibodies reactive with endotoxin core.

The bacteria described above were grown overnight at 32° C. on tryptic soy agar slants (Difco, Detroit, Mich.) and then inoculated into 4 liter-capacity Fernbach flasks containing 1000 ml of tryptic soy broth (Difco). These cultures were incubated, with shaking, at 32° C. for 18 hr, the cells removed by centrifugation, washed twice with 0.15 M NaCl and weighed. The bacteria were then suspended at a concentration of 0.2 μg/ml in 0.05 M Tris (hydroxymethyl)aminomethane-hydrochloride buffer, pH 9.0, with 0.15 M NaCl, sonicated with a large probe (Sonicator Cell Disruptor, Heat Systems-Ultrasonics, Inc., Plainview, N.Y.) at maximum setting for a total of 10 min. After centrifugation the pellet was resuspended and the sonication repeated. The fragmented cells were suspended at a concentration of 0.4 μg/ml in distilled water and heated at 70° C. in a water bath; then an equal volume of 90% re-crystalized phenol (pH 7.0) was added, and the mixture incubated at 70° C. with constant stirring for 15 min (Westphal et al. *Z. Naturforsch,* 7b:148, 1952, which is hereby incorporated by reference). The mixture was then cooled to 4° C., centrifuged at 10,000 rpm for 10 min, the aqueous phase saved, and the phenol phase reextracted with an equal volume of water as described above. The phenol phase and denatured protein at the phenol-water interface were discarded and the lipopolysaccharide-containing aqueous phases combined. The lipopolysaccharide suspension was then placed in a separatory funnel, extracted with anhydrous diethyl ether (2:1 ratio of ether to lipopolysaccharide suspension), and the aqueous phase saved. Water was added to the ether phase in the amount removed, the mixture shaken, and the aqueous phase again removed. The combined aqueous phases were re-extracted overnight with additional ether. Excess ether was removed from the final aqueous phase by bubbling nitrogen through the solution. RNAse (Type II-A, Sigma Chemical Co., St. Louis, Mo.) was added to the lipopolysaccharide suspension at a concentration of 2 Kunitz units/ml. The mixture was then dialyzed at room temperature against multiple changes of 0.01 M Tris-acetate, pH 7.5, with 0.1 M NaCl and 1.0 mM $NaN_3$ until the optical density of the dialysate, monitored in the 230-300 nm range reached 0. The lipopolysaccharide suspension was next dialyzed against water in the cold overnight. DNAse (Type II, Sigma) was added at a concentration of 2 Kunitz units/ml, and the suspension dialyzed against repeated changes of 0.1 M NaCl with 5 mM $MgSO_4$ and 1 mM $NaN_3$ until the absorbance of the dialysate reached 0 in the 230-300 nm range. The lipopolysaccharide suspension was then dialyzed against cold water overnight, pronase (Type V, Sigma) added in a concentration of 1 Kunitz unit/100 ml, the solution dialyzed overnight against several changes of 0.01 M Trisacetate pH 7.5, followed by dialysis against multiple changes of cold water over several days. The lipopolysaccharide suspension was lyophilized and weighed.

Whereas in this case endotoxin core was prepared as described above, alternative purification procedures, such as that described by Galanos et al. (*European Journal of Biochemistry,* 9:245, 1969), which is hereby incorporated by reference, might also be employed for the isolation of endotoxin core. In certain circumstances it might even be advisable to employ other purification methods, such as that of Galanos et al., in order to maximize the yield of endotoxin core or to retain or more favorably "present" particular antigenic sites or epitopes toward which monoclonal antibodies are sought.

Purified *E. coli* J5 endotoxin core contained <1% protein as determined by the Coomassie Blue-binding method of Bradford (Bradford, M.M., *Analytical Biochemistry,* 72:248, 1976) and corroborated by amino acid analysis. Neutral sugar analysis by reverse-phase chromatography using a cation exchange resin in the $Li^+$ form with 90% ethanol as eluent revealed the presence of heptose and glucose, ± galactose, and no colitose, the latter being a unique sugar contained in the 0-specific side chains of the smooth *E. coli* 0111:B4 parent strain. These data confirmed an incomplete core structure corresponding to the Rc chemotype of Salmonella (Luderitz, O., et al, *Bacterological Reviews,* 30:192, 1966; Wilkinson, S.G., In *Surface Carbohydrates of the Prokaryotic Cell,* I.W. Sutherland, editor, Academic Press, New York, 1977, pp 97-171). Electrophoresis in 14% SDS polyacrylamide gel, followed by silver staining (FIG. 1), revealed a single, broad, fast-migrating band (J5) similar in mobility to core structures from other simultaneously run lipopolysaccharides (S, Ra, Rd); regularly spaced slower migrating bands characteristic of intact smooth lipopolysaccharide (S) were absent (see Tsai, C., Frasch, C.E., *Analytical Biochemistry,* 119:115, 1982). As depicted in FIG. 1, the sample designated "S" contained 5 μg of lipopolysaccharide from the smooth *Escherichia coli* 0111:B4 wild type strain; "$R_a$" contained 0.2 μg of lipopolysaccharide from the *E. coli* PL2 rough mutant, characterized by a complete core structure corresponding to the $R_a$ chemotype of Salmonella; "$R_d$" contained 0.2 μg of lipopolysaccharide from the *E. coli* PL2-CL29 rough mutant, characterized by an incomplete core structure corresponding to the $R_d$ chemotype of Salmonella; and "J5" contained 0.2 μg of lipopolysaccharide from the uridine diphosphate 4-epimerase-deficient mutant designated J5, which is derived from the *E. coli* 0111:B4 parent strain, the incomplete core structure of which corresponds to the $R_c$ chemotype of Salmonella. The purity and functional integrity of endotoxin core prepared from J5 were confirmed in mitogenesis assays employing spleen cells from high- and low-responder C3H/FeJ and C3H/HeJ mice, respectively. Mitogenic responses to purified endotoxin core were comparable to those induced by highly purified lipopolysaccharide from the smooth *E. coli* K235 strain (Skidmore, B.J., *Journal of Experimental Medicine*, 142:1488, 1975). These included high responses by C3H/FeJ spleen cells, low or absent responses by C3H/HeJ spleen cells, and complete abrogation of mitogenic activity following incubation of endotoxin core with polymyxin B.

Antibodies to purified endotoxin core were quantified using an enzyme-linked immunosorbent assay (ELISA). Purified endotoxin core was dissolved at a concentration of 25 μg/ml in coating buffer (15 mM $Na_2CO_3$, 30mM $NaHCO_3$, 3 mM $NaN_3$, pH 9.55) and dispensed in 50 μl aliquots into 96-well polystyrene microtiter plates (Dynatech Laboratories, Inc., Alexandria, Va.). After overnight incubation at 4° C., the endotoxin suspension was removed and the wells washed five times with PBS-Tween (150 mM NaCl, 6 mM $Na_2HPO_4$, 1 mM $KH_2PO_4$, 3 mm $NaN_3$, and 0.5 ml/l Tween-20). 50 μl test samples were added to wells, the plates incubated at 4° C. for 30 min and then washed five times with PBS-Tween. The final three steps, separated by PBS-Tween washes, were as follows: addition of 50 μl of rabbit anti-mouse kappa-chain (Cappel Laboratories, Cochransville, Pa.) diluted 1:500 and previously absorbed with whole *E. coli* J5 cells, followed by incubation at 4° C. for 30 min; addition of 50 μl of goat anti-rabbit IgG-alkaline phosphatase conjugate (Sigma) diluted 1:250 and incubation at 4° C. for 30 min; addition of 50 μl of p-nitrophenylphosphate (Sigma-104) substrate, 1 mg/ml in 10% diethanolamine, pH 9.8, and incubation at 25° C. for 60 min. Absorbance was read at 405 nm in a Titertek Multiskan micro-ELISA spectrophotometer (Flow Laboratories, Vienna, Va.).

The assay was later standardized with affinity-purified endotoxin core-specific immunoglobulin prepared from high-titered mouse ascites fluid. Test sample dilutions were used which yielded an absorbance closest to the mid-point of the standard curve, and concentrations of specific antibody calculated by least squares method from the standard curve. The sensitivity of the assay was 0.02 μg/ml and reproducibility among triplicate samples averaged ±4%.

The following is a description of how to prepare self-reproducing carrier cells, which in this case were mouse hybridomas, that contain genes coding for the production of monoclonal antibodies reactive with endotoxin core, and how clones of these carrier cells might be made to reproduce on a large scale, and how monoclonal antibodies might be obtained from these clones.

We describe how spleen cells (B lymphocytes) obtained from mice previously immunized with J5 endotoxin core were fused with mouse plasmacytoma cells, resulting in so-called hybridomas, and how cells from these hybridomas which secreted monoclonal antibodies to endotoxin core were cloned. We also demonstrate how two distinct hybridoma clones (J5-1 and J5-2), derived from two separate fusion experiments, were reproduced on a large scale employing both in vitro and in vivo techniques, and how monclonal antibodies reactive with endotoxin core were obtained from these self-reproducing carrier cells in large, usable quantities.

Six week-old female BALB/c mice were injected intraperitoneally at three weekly intervals with 50 μg of purified J5 endotoxin core suspended in 0.15 M NaCl. The donor mice were killed by cervical dislocation three days following the last immunization; the spleen was removed aseptically and placed in a 35 mm plastic Petri dish with 5 ml of cold RPMI 1640 medium. The spleen was dissociated into a single cell suspension, the cells were washed twice with cold RPMI 1640, and resuspended in the same medium.

An immunoglobulin non-secreting mouse plasmacytoma cell line (P3-X63-Ag8.653) deficient in the enzyme hypoxanthineguanine phophoribosyl transferase (HGPRT-, EC 2.4.2.8), as disclosed by Kearney (*Journal of Immunology*, 123:1548, 1979), which is hereby incorporated by reference, was used as the fusion partner. This cell line is available from the American Type Culture Collection, Rockville, Md., where it is designated ATCC CRL-1580. The plasmacytoma cell line was maintained in RPMI 1640 medium containing 10% fetal bovine serum and further supplemented with 2 mM L-glutamine, 1% sodium pyruvate, 1% non-essential amino acids, 100 IU/ml penicillin and 100 μg/ml streptomycin. For three days prior to fusion, 0.1 mM 8-azaguanine was added to the plasmacytoma cells in order to kill any HGPRT+revertants. On the day of fusion, the plasmacytoma cells were harvested from 75 cm² culture flasks, washed once and resuspended in serum-free RPMI 1640 medium. The plasmacytoma and previously harvested spleen cells were counted and their viability assessed by Trypan blue dye exclusion.

The fusion technique was modified from that of Gefter et al. (*Somatic Cell Genetics*, 3:231, 1977), which is hereby incorporated by reference into this description. Described below is the fusion experiment which yielded the J5-1 hybridoma clone; a second fusion experiment performed in an identical manner produced the J5-2 hybridoma clone. To a sterile 50 ml conical plastic tube was added $1.0 \times 10^8$ spleen cells and $1.0 \times 10^7$ plasmacytoma cells. The plasmacytoma-spleen cell suspension was centrifuged at 250×g for 10 min at room temperature and the medium then decanted to near dryness. The cell pellet was loosened gently by flicking and 1 ml of 50% polyethylene glycol (MW 1400) in RPMI 1640, without serum, was added in drops over 45 seconds. The tube was gently agitated during this process. One minute later, another 2 ml of RPMI 1640 was added over 2 min. An additional 20 ml of RPMI 1640 was added over the next 2 min, and the cells pelleted by centrifugation at 250×g for 10 min at room temperature.

The fluid was decanted and 40 ml of enriched selection medium was added. This medium was composed of Dulbecco's MEM containing 10% fetal bovine serum and supplemented with 2 mM L-glutamine, 1% sodium pyruvate, 1% non-essential amino acids, 100 IU/ml penicillin, 100 μg/ml streptomycin, 1 mM oxaloacetic acid, 10% NCTC 109, and 0.2 μg/ml bovine pancreatic insulin. The medium also contained $1.0 \times 10^{-4}$ M hypoxanthine, $4.0 \times 10^{-7}$ M aminopterin, and $1.6 \times 10^{-5}$ M thymidine (HAT). Aminopterin is toxic for cells that lack the enzyme HGPRT and therefore kills all unfused plasmacytoma cells. Fused cells (hybridomas) survive in HAT because they obtain HGPRT from the B lymphocyte (spleen cell) fusion partner.

Aliquots of 0.2 ml containing $5.0 \times 10^5$ cells were transferred from the above mixture into individual wells of several sterile flat-bottomed microtiter plates. The plates were incubated at 37° C. in a humidified atmosphere consisting of 6% $CO_2$ and 94% air. Fresh selection medium was added on alternate days for the next 11 days. On day 11, the microculture supernatants were tested by the ELISA assay described above for antibodies reactive with *E. coli* J5 endotoxin core. Positive cultures were expanded in number and transferred to 35 $cm^2$ flasks. The medium from these cultures was retested, and those maintaining antibody secretion were cryopreserved and stored at $-179°$ C. in liquid nitrogen vapor phase.

One of the positive hybridoma cultures described above, and one derived from the second fusion experiment, were selected for cloning by limiting dilution. 100 µl aliquots containing 0-1 cells were transferred to several hundred individual wells in sterile flat-bottomed microtiter plates that had been previously seeded with $1.0 \times 10^5$ mouse tumor macrophages (P388D1) per well. The macrophages are available from several commercial sources. They serve as "feeder" cells for the hybridomas, and were irradiated (Cobalt 60 source, 1000 Rads) prior to use to prevent multiplication in culture. After 14 days, the cloned cultures were tested again by ELISA assay for antibodies reactive with endotoxin core, and one positive clone from each of the two parental cultures was selected for further study. These cloned hybridomas, designated J5-1 (ATCC HB 8297) and J5-2 (ATCC HB 8298) were expanded in numbers, cryopreserved, and stored in the same manner as the parental cell lines from which they were derived.

Two methods were employed to demonstrate that the production of useful quantities of monoclonal antibodies from the J5-1 and J5-2 hybridomas was possible. An in vitro method utilized stationary cultures of both cell lines grown in 75 $cm^2$ culture flasks containing RPMI 1640 medium supplemented as described above. It was convenient, after 5-7 days of incubation at 37° C. under 6% $CO_2$, to obtain 1-2 liters of culture fluid containing approximately 10 µg/ml of J5-1 antibody and 1 µg/ml of the J5-2 antibody.

A second, in vivo method for obtaining large amounts of monoclonal antibodies involved the adaptation of the J5-1 and J5-2 cell lines to growth as "ascites" tumors. Female BALB/c mice were "primed" by intraperitoneal injection of 0.5 ml of pristane (2,6,10,14-tetramethylpentadecane). Pristane is a sterile irritant which elicits a serious secretion ("ascites") in the peritoneal cavity of mice which acts as a growth medium. Approximately 7-10 days following the pristane injection, aliquots containing $1.0 \times 10^6$ actively growing hybridoma cells harvested from in vitro cultures (described above) were inoculated into the peritoneal cavities of primed mice. Hybridoma cells were serially passaged at 1-2 week ntervals to freshly primed mice. After 3-4 such passages, the J5-1 and J5-2 hybridomas became well-adapted ascites tumors, growing rapidly in the fluid microenvironment of the mouse peritoneal cavity and secreting large quantities (e.g., 2-10 mg/ml) of monoclonal antibodies reactive with endotoxin core. Routinely, 20-30 ml of ascites fluid was removed from each mouse by aspiration. The antibody-secreting tumor cells were separated from the antibody-containing fluid phase and reinjected into other primed mice, and the process was repeated.

A third method that can be employed for large scale production of monoclonal antibodies reactive with endotoxin core is made possible by, and requires, the prior preparation of the hybridomas and monoclonal antibodies of this invention. According to this method, genes that code for monoclonal antibodies reactive with endotoxin core are transferred from the hybridomas which produce them to more rapidly reproducing microorganisms such as bacteria or yeast, and the antibody product of these genes recovered from the microorganism itself or the medium in which the microorganism is grown. This method is based on recombinant DNA technology as originally described by Cohen et al. in the *Proceedings of the National Academy of Sciences, USA*, 70:3240, 1973, which is hereby incorporated by reference into this description (see also U.S. Pat. No. 4,237,224). The techniques used to accomplish this method have been described by Ullrich et al., *Science*, 196:1313, 1977, and Goeddel et al., *Proceedings of the National Academy of Sciences, USA*, 76:106, 1979, who cloned the genes for rat insulin and human growth hormone, respectively, into bacteria, and by Hitzeman et al., *Nature* (London), 293:717, 1981, who transferred the human α-1 interferon gene into yeast. These publications are hereby incorporated by reference into this description.

The clones designated J5-1 (ATCC HB 8297) and J5-2 (ATCC HB 8298) were derived from two distinct hybridoma cell lines and were prepared as described above. Both clones are stable in tissue culture; J5-1 (ATCC HB 8297) produces approximately 10 µg/ml of antibody protein and J5-2 (ATCC HB 8298) secretes about 1 µg/ml. Both clones have also been adapted as mouse ascites tumors, and produce 2-10 mg/ml of antibody in this system.

The immunoglobulins (antibodies) produced by the J5-1 and J5-2 hybridomas are both of the IgG1 isotype and subclass, as demonstrated by double gel immunodiffusion (Ouchterlony) analysis employing immunopurified anti-immunoglobulin class- and subclass-specific reagents. The monoclonality of the J5-1 and J5-2 antibodies, previously insured by re-cloning the hybridomas which produced them, was confirmed by SDS-polyacrylamide gel electrophoresis and autoradiography employing biosynthetically labeled antibody samples.

Figure 2:
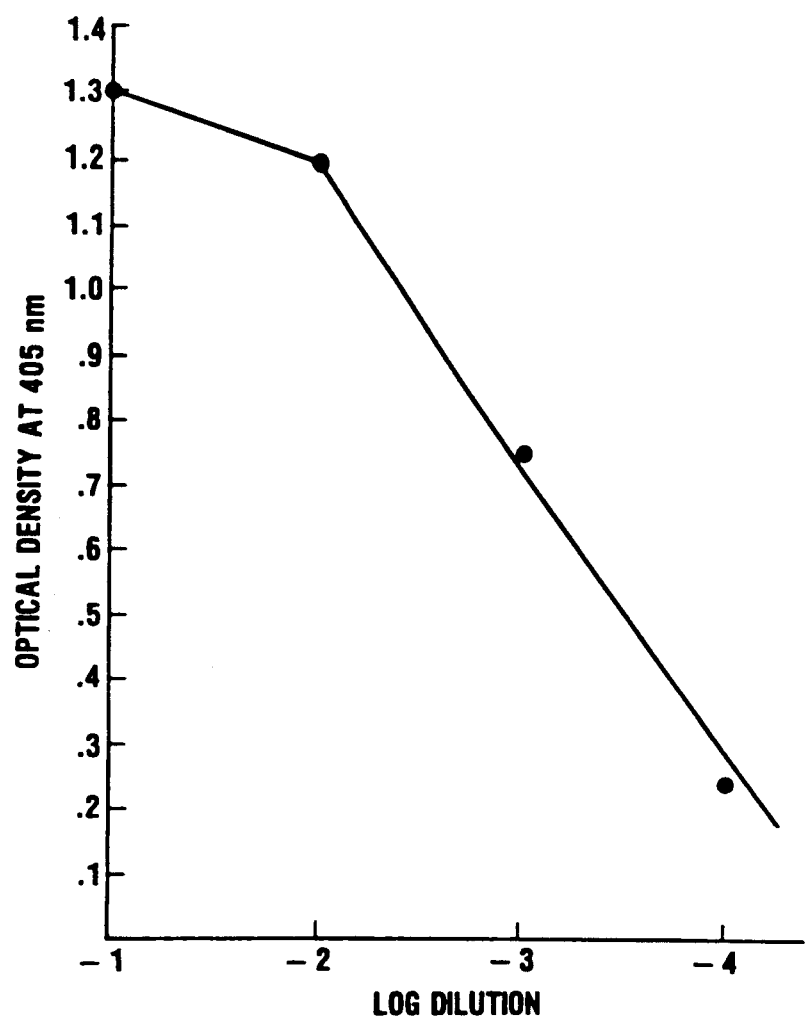
FIG. 2 depicts the binding in an ELISA assay of monoclonal antibodies obtained from a J5-1 hybridoma culture supernatant with purified *Escherichia coli* J5 endotoxin core.

The binding of J5-1 and J5-2 antibodies by endotoxin core was examined using the enzyme-linked immunosorbent assay (ELISA) described above. Purified *E. coli* J5 core antigen was used to coat the wells of microtiter plates in which the assays were performed and the resulting color reactions measured. A representative "binding curve", shown in FIG. 2, was obtained when dilutions of ammonium sulfate precipitated and redissolved protein from a J5-1 hybridoma culture supernatant were assayed by ELISA. A similar binding curve, but with a slightly different slope, was obtained upon assay of J5-2 culture supernatant.

Figure 3:
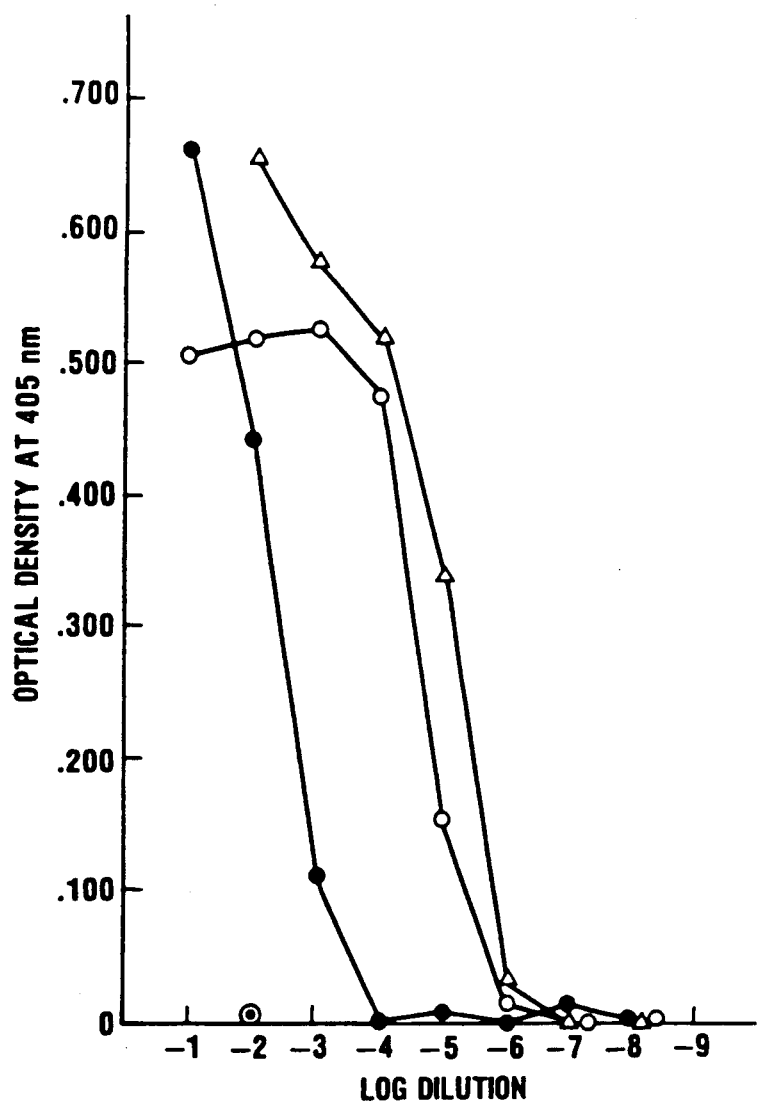
FIG. 3 shows the binding in an ELISA assay of monoclonal antibodies produced by a J5-1 ascites tumor with purified *Escherichia coli* J5 endotoxin core.

Shown in FIG. 3 are binding curves obtained by ELISA assay of ascites fluid from a mouse which had been intraperitoneally injected with J5-1 antibody-secreting ascites tumor. The parallel binding curves in this figure were obtained by assaying serial dilutions of untreated ascites fluid (○), ammonium sulfate-precipitated and redissolved protein from the same ascites fluid (Δ), and affinity purified J5-1 monoclonal antibodies (●) prepared by passing the ascites fluid over a Sepharose 4B column to which purified *E. coli* J5 endotoxin had been previously bound. The specificity of J5-1 antibodies produced in ascites fluid was indicated by the results of this immunoabsorption procedure, and by the observed removal of antibody activity from material absorbed with purified endotoxin core ((○) in FIG. 3) Antibody activity was detected by ELISA in approximately 1000 times higher dilutions of J5-1 ascites fluid compared with J5-1 culture supernatants, reflecting the higher antibody concentrations obtained by the in vivo production method. Similar amounts of antibody and similar binding curves were obtained in the case of ascites fluid produced by the J5-2 hybridoma.

Figure 4:
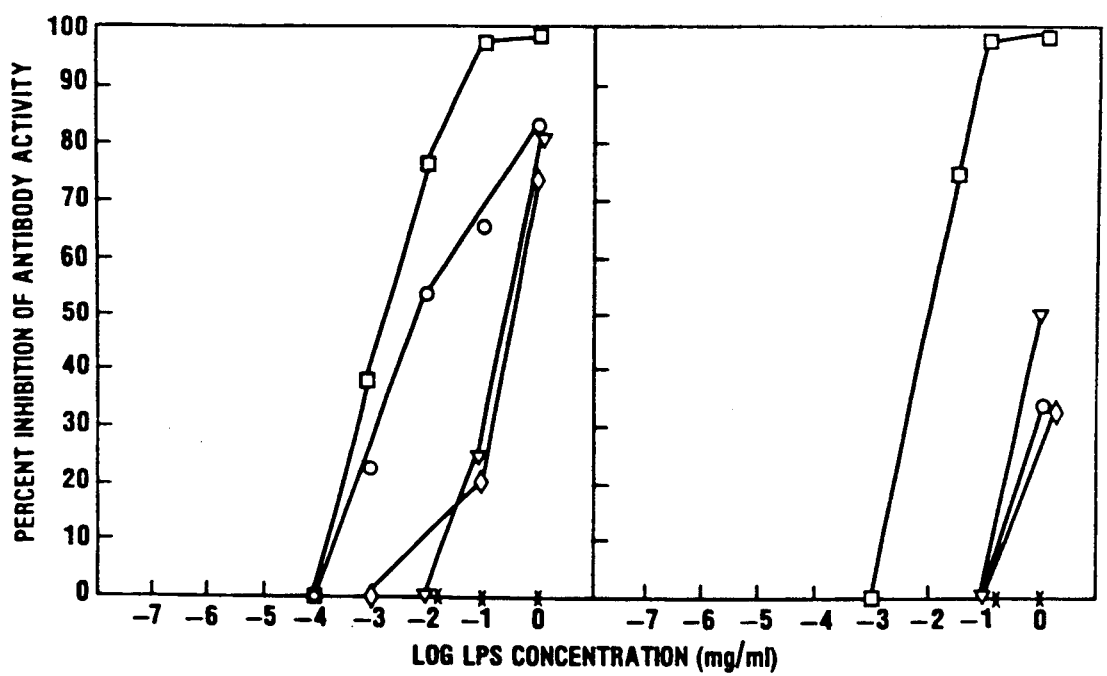
FIG. 4 is a depiction of the results of a competitive inhibition ELISA assay illustrating a concentration-dependent inhibition of the specific binding activities of the J5-1 and J5-2 monoclonal antibodies by homologous and heterologous endotoxins.

Two salient features of monoclonal antibodies reactive with endotoxin core are their specificity for, as well as their cross-reactivity with, any part of the endotoxin core structures of different Gram-negative bacteria. These characteristics were confirmed by a competitive inhibition ELISA assay of antibodies produced by both the J5-1 (left panel, in FIG. 4) and J5-2 (right panel in FIG. 4) hybridomas. Preincubation of both antibodies with purified *E. coli* J5 endotoxin core (□) abolished their reactivity in the ELISA assay in a dose-dependent manner. This confirmed the specificity of both antibodies for endotoxin core. In addition, it was shown (FIG. 4) that preincubation of J5-1 and J5-2 antibodies with other, heterologous endotoxins, including those obtained from both "rough" and "smooth" organisms and representing different species and genera of bacteria (such as *Escherichia coli* K235 (▽), *Pseudomonas aeruginosa* Fisher Type 2 (○), and the *Salmonella minnesota* R595 Re mutant (◊), also inhibited the reactivity of both antibodies in the ELISA assay. These data, confirmed by double gel immunodiffusion analysis, establish the cross-reactivity of both monoclonal antibodies with endotoxins from a variety of sources.

The functional activity of the J5-1 and J5-2 monoclonal antibodies was evaluated in an in vitro assay which measures the ability of endotoxin to stimulate the proliferation and differentiation of B lymphocytes. This mitogenic activity is shared by most endotoxins and is mediated by the lipid A moiety of the endotoxin core. Lipid A also mediates most other biological activities of endotoxins. It is convenient to quantify mitogenic activity in a highly sensitive and widely used in vitro assay system which employs mouse spleen cells.

We used such an in vitro assay to evaluate the ability of J5-1 and J5-2 monoclonal antibodies to neutralize the mitogenic activity of endotoxins from *E. coli* (J5) and other Gram-negative bacteria. Preincubation of homologous and heterologous endotoxins with J5-1 antibodies caused an inhibition of subsequent mitogenic activity manifested by a decrease in $^3$H-thymidine uptake by mouse spleen cells exposed to the endotoxins in tissue culture for 48 h, as shown in the following table.

TABLE 1

Neutralization of Lipopolysaccharide-Induced B Cell Mitogenesis by Monoclonal Antibody Produced by the J5-1 Hybridoma

| Lipopolysaccharide Source | CPM + SEM | |
|---|---|---|
| | Without J5-1 Antibody | With J5-1 Antibody |
| *E. coli* 0111:B4 (J5 mutant) | 19,456 ± 1,699 | 3,084 ± 301 |
| *E. coli* K235 | 16,782 ± 481 | 2,755 ± 383 |
| *P. aeruginosa* (Fisher Type 2) | 25,412 ± 1,034 | 1,848 ± 431 |

TABLE 1-continued

Neutralization of Lipopolysaccharide-Induced B Cell Mitogenesis by Monoclonal Antibody Produced by the J5-1 Hybridoma

| Lipopolysaccharide Source | CPM + SEM | |
|---|---|---|
| | Without J5-1 Antibody | With J5-1 Antibody |
| Media control | 1,685 ± 162 | 1,828 ± 290 |

The specificity of the above inhibition was established by the observation that endotoxin-induced B cell mitogenesis was not affected by monoclonal antibodies of the IgG1 subclass directed toward antigens other than endotoxin core, and by the fact that neutralization of endotoxin-induced mitogenesis by J5-1 antibodies was demonstrable with endotoxin-responsive B lymphocytes from C3H/Fej mice but not with endotoxin-unresponsive B lymphocytes from C3H/Hej mice.

The data presented in Table 1 thus establish the fact that monoclonal antibodies produced by the J5-1 hybridoma neutralize a biological activity of endotoxin. These data also confirm the cross-reactivity of J5-1 antibodies with endotoxins derived from different genera and species of Gram-egative bacteria. Similar data were obtained with antibodies produced by the J5-2 clone which also specifically inhibited the mitogenic activity of homologous and heterologous endotoxins.

Although the antibodies secreted by the J5-1 and J5-2 hybridomas were similar in their activities, they produced binding curves with distinctive slopes and their endotoxin-neutralizing capacities were quantitatively different, suggesting that the two monoclonal antibodies are directed toward two separate sites (epitopes) on the endotoxin core structure. This, in turn, indicates the existence of multiple, distinct B lymphocyte clones producing monoclonal antibodies directed at different epitopes, having different binding affinities, and perhaps different functional activities, yet all having in common their reactivity with endotoxin core. The J5-1 and J5-2 antibodies thus represent but two examples of this larger "set" of antibodies defined by their reactivity with any part of endotoxin core. The present invention embraces this entire set of antibodies, as well as the genes which code for them, the self-reproducing carrier cells which produce them, and so on.

We next evaluated the cross-protective activity of J5-1 monoclonal antibodies against an actual Gram-negative bacterial infection caused by an organism genetically distinct from the *E. coli* J5 strain. Monoclonal antibody obtained by ammonium sulfate precipitation of the culture supernatant from an in vitro culture of the J5-1 hybridoma was injected intravenously into 20g Swiss-Webster mice at a dose of 20 μg/mouse. Control animals received bovine serum albumin (BSA) in the same dose. Eighteen hours later, the mice underwent a 10 sec, 6.25 cm$^2$ flame burn followed by subcutaneous inoculation at the burn site of 6, 10-fold dilutions, 5 mice per dilution, of washed, log phase *Pseudomonas aeruginosa* (Fisher Type 1) bacteria. Deaths were recorded for three days and median lethal dose (LD$_{50}$) of bacteria calculated by the method of Spearman-Karber (D. J. Finney, *Statistical Method in Biological Assay*, Third Edition, Macmillan, New York, 1978, pp. 394–401) for the J5-1 and control groups, respectively. The resulting data are shown below.

TABLE 2

Protective Activity of Monoclonal Antibody Produced by the J5-1 Hybridoma Against *Pseudomonas aeruginosa* Burn Infections in Mice

| Treatment | Inoculum Size (CFU) | | | | | | $LD_{50}$ |
|---|---|---|---|---|---|---|---|
| | $10^8$ | $10^7$ | $10^6$ | $10^5$ | $10^4$ | $10^3$ | |
| BSA (control) | 0* | 0 | 0 | 80 | 80 | 100 | $1.3 \times 10^5$ |
| Anti-J5 | 0* | 0 | 60 | 100 | 100 | 100 | $1.4 \times 10^6$ |

*Percent survival, five mice per group.

Protection was observed in mice that received J5-1 monoclonal antibody, as indicated by a greater than 10-fold increase in the size of the bacterial innoculum required to kill 50% of the animals in this group. These and similar studies demonstrate the in vivo effectiveness of monoclonal antibodies to endotoxin core in preventing death due to a Gram-negative bacterial infection. In this case, monoclonal antibody to the endotoxin core of the *E. coli* J5 strain exhibited protective activity against a lethal infection caused by a *Pseudomonas aeruginosa* organism, thus demonstrating the cross-protective efficacy of this antibody against heterologous Gram-negative bacteria.

In summary, monoclonal antibodies reactive with endotoxin core were prepared by fusing mouse B lymphocytes with plasmacytoma cells and selecting for hybridomas which secreted these specific antibodies. Two distinct monoclonal antibodies reactive with endotoxin core, derived from different hybridoma clones resulting from two separate fusions, were mass-produced in tissue culture and in mouse ascites, thus illustrating the feasibility of preparing these antibodies in large quantities by in vitro and in vivo techniques. The two monoclonal antibodies thus produced, which we designated J5-1 and J5-2, were characterized as described above. Their specific reactivity with homologous and heterologous endotoxins was demonstrated in a binding assay; their ability to neutralize a lipid A-mediated biological activity of endotoxins derived from different Gram-negative bacteria was indicated by the results of mitogenesis assays; and their cross-protective activity against Gram-negative bacterial infections was suggested by passive protection studies carried out in a murine Pseudomonas burn-wound sepsis model.

The novel feature of this invention derives from the selection and reproduction of genes specifying the production of monoclonal antibodies reactive with any part of endotoxin core, as that term is broadly defined at page 3 of the specification. By means of example only, the invention includes monoclonal antibodies that are reactive with any part of endotoxin core, such as the lipid A moiety or its substituents, or antigenic sites, such as core sugars or their substituents, closely associated with but distinct from the lipid A moiety. In addition, the invention is directed to the actual production of these antibodies. The particular methods illustrated above, and the specific antibodies which resulted, are merely examples of how the invention might be conveniently practiced and how appropriate products might be obtained. Any methods or techniques leading to the propagation of genes specifying the production of monoclonal antibodies reactive with any part of endotoxin core, and any antibodies so produced, are embraced by this invention.

The scope of the invention includes, in addition to the monoclonal antibodies themselves and methods of preparation, in vitro and in vivo processes for producing the antibodies, immunodiagnostic methods and compositions employing the antibodies, immunoprophylactic and therapeutic methods and compositions employing the antibodies, research methods and compositions employing the antibodies, purification methods and compositions employing the antibodies, and other methods and compositions employing the antibodies, such methods and compositions predicated upon the specific interaction between the antibodies and endotoxin core.

For the purpose of illustrating the invention, the preceding examples were primarily in terms of hybridomas, and in the case of the examples actually illustrated, these hybridomas resulted from the fusion of mouse B lymphocytes and mouse plasmacytoma cells. However, the essential and novel feature of the present invention is the employment of genes coding for the production of specific antibodies reactive with any part of endotoxin core and the preparation, employing these genes, of monoclonal antibodies reactive with any part of endotoxin core. As indicated, the genes employed and the carrier cells employed may originate from any animal species, including man, as long as they result in the production of monoclonal antibodies reactive with any part of endotoxin core. Likewise, any in vitro or in vivo methods and compositions may be employed for the large-scale production of these antibodies as long as monoclonal antibodies reactive with any part of endotoxin core result from their use.

When carrier cells are employed in the invention, they are principally characterized by being self-reproducible, and by having genes that code for the production of monoclonal antibodies reactive with any part of endotoxin core. As illustrated in connection with other monoclonal antibodies, these carrier cells can be cell lines such as human-human (Hunter et al., *Lancet*, 2:798, 1982), human-nonhuman (Nowinski et al., *Science*, 210:537, 1980), or wholly nonhuman hybridomas (Kohler and Milstein, *Nature*, 265:495, 1975) or transformed parental lymphoid cells (Steinitz et al., *Nature*, 269:420, 1977). Each of the above four publications is hereby incorporated by reference. These references, in combination with the detailed description of the patent, would enable a person skilled in the art to prepare carrier cells of a human or nonhuman animal species containing genes of human or nonhuman origin that code for the production of monoclonal antibodies reactive with endotoxin core. For example, human-human hybridomas producing human antibodies reactive with endotoxin core can be prepared in a manner similar to that described above for mouse hybridomas except that spleen cells or peripheral blood lymphocytes obtained from human donors immunized with or previously exposed to endotoxin core and a human myeloma fusion partner such as the HFB-1 cell line (Hunter et al., *Lancet*, 2:798, 1982) are substituted for mouse spleen and plasmacytoma cells, respectively. Similarly, spleen cells or peripheral blood lymphocytes obtained from human donors immunized with or previously exposed to endotoxin core can be fused with a mouse myeloma fusion partner such as the P3-x63-Ag8.653 cell line (described above in the preparation of a mouse-mouse hybridoma), yielding a self-reproducing human-mouse hybridoma which produces human monoclonal antibody reactive with endotoxin core.

Another approach to the preparation of self-reproducing carrier cells that secrete human or nonhuman monoclonal antibodies reactive with endotoxin core involves virus transformation of the appropriate B lymphocyte clone. Steinitz et al. (*Nature*, 269:420, 1977) employed such a procedure to prepare specific human antibody to the synthetic hapten NNP (4-hydroxy-3,5-dinitrophenacetic acid). According to this technique, for example, peripheral blood lymphocytes from human donors immunized with or previously exposed to purified endotoxin core can be isolated on Ficoll-Hypaque. A B lymphocyte population enriched in respect to the production of antibodies reactive with endotoxin core is prepared by a method such as rosetting on endotoxin core-coated erythrocytes. Rosetted cells are separated from non-rosetted cells by centrifugation on Ficoll-Hypaque, placed in tissue culture medium, and infected with Epstein-Barr Virus (EBV) obtained, for example, from supernatants from mycoplasma-free B95-8 cell cultures. The EBV-infected B lymphocytes are transformed into continuously proliferating cell lines ("immortalized"), and those secreting antibodies reactive with endotoxin core are identified by ELISA or other appropriate assay and cloned, essentially as described above for hybridomas. The permanent cell lines thus obtained, which produce human monoclonal antibodies reactive with endotoxin core, can be grown, and antibody production maintained indefinitely, in RPMI 1640 plus 20% fetal calf serum or comparable medium.

The procedures outlined above for obtaining human or nonhuman monoclonal antibodies reactive with endotoxin core employing B lymphocytes fused with tumor cells (hybridomas) and virus-transformed B lymphocytes are similar in all respects except the method by which "immortalization" of the appropriate B lymphocyte clone is achieved. Both techniques entail preparation of purified endotoxin core, immunization of a B lymphocyte donor, selection and cloning of self-reproducing carrier cells containing genes specifying the production of monoclonal antibodies reactive with endotoxin core, growth of these cells in continuous culture, and recovery of the monoclonal antibodies produced.

Yet another approach useful for the preparation of self-reproducing carrier cells containing genes specifying the production of monoclonal antibodies reactive with endotoxin core was described earlier in the specification in connection with the large-scale production of these antibodies. This method, which involves the cloning of genes coding for the production of antibodies reactive with endotoxin core into rapidly dividing microorganisms employing recombinant DNA techniques, requires the prior existence of self-reproducing carrier cells (e.g., hybridomas) that contain these genes and that produce the monoclonal antibodies of this invention.

Just as a variety of different systems and methods might be employed to select for and reproduce genes specifying the production of monoclonal antibodies reactive with endotoxin core, so might a variety of antibodies result from these measures that are distinct from the two antibodies illustrated above yet still clearly within the definition of this invention. Once again, the salient feature of such antibodies, for the purposes of this invention, besides their monoclonality, is their reactivity with any part of endotoxin core. Thus, the invention includes any monoclonal antibody that reacts with any part of endotoxin core, regardless of species of origin, isotype, molecular specificity, affinity, method of production (whether in vitro or in vivo), or type of carrier cell employed in its production.

As previously discussed, some of the major advantages of monoclonal over polyclonal antibodies reactive with endotoxin core derive from their exquisite specificity and the virtually limitless quantities in which they can be produced. These features of monoclonal antibodies to endotoxin core, together with their demonstrated cross-reactivity with endotoxins from diverse Gram-negative bacteria, their ability to neutralize the biological activity of endotoxins, and their protective activity upon administration to animals with Gram-negative infections, suggest a number of important applications and convenient forms in which the antibodies might be used. These applications fall into four major areas, as outlined below.

The monoclonal antibodies of this invention are reagents that may be used to identify endotoxin, or microorganisms bearing endotoxin, in the tissues or body fluids of patients (or animals) infected with these microorganisms, thus permitting rapid and accurate immunological diagnosis of such infections. This form of diagnosis is made possible, in part, by the great specificity of the monoclonal antibodies of this invention compared with conventional, polyclonal antibodies reactive with endotoxin core. A further advantage of immunological diagnosis utilizing monoclonal antibodies is the speed with which this form of diagnosis can be carried out (e.g., hours) compared with diagnosis based on standard microbiological or cultural methods (e.g., days). A still further advantage of immunological diagnosis employing monoclonal antibodies is that prior antibiotic treatment of an infected patient does not necessarily interfere with or prevent diagnosis as it may in the case of standard microbiological diagnostic procedures.

Monoclonal antibodies reactive with endotoxin core are also useful for the immunological detection of endotoxin or endotoxin-bearing microorganisms present as contaminants in water, biologicals, pharmaceuticals or other materials. Detection is convenient, rapid, sensitive, and highly specific. Furthermore, immunological detection of endotoxin employing monoclonal antibodies to endotoxin core is far more specific than the currently employed limulus lysate assay for endotoxin or assays which employ polyclonal antibodies.

A diagnostic composition, or composition useful for detection of endotoxin, in accordance with the present invention, contains a concentration of the antibody effective to diagnose an infection, detect endotoxin, or demonstrate endotoxin-bearing microorganisms. The antibody can be packaged and sold in freeze-dried or other acceptable form for diagnostic use. It may be mixed with a suitable carrier, attached to an appropriate solid phase (e.g., latex particle, protein A-bearing *Staphylococcus aureus*, or plastic microtiter plate), conjugated with an enzyme or dye, or radiolabeled, depending on what immunological method is employed.

In a diagnostic or detection method in accordance with this invention, the antibodies of the present invention may be mixed with a sample of body fluid or blood or tissue removed from a person (or animal) infected with an endotoxin-bearing microorganism, or sample of water, biological, pharmaceutical or other material contaminated with endotoxin or an endotoxin-bearing microorganism, and the degree of reaction in the resulting mixture measured. The amount of antibody required to carry out the diagnosis or accomplish the detection depends upon factors that include the amount of sample to be tested, the amount of endotoxin or number of microorganisms present, and the type of assay used. The monoclonal antibodies of the present invention can be employed for diagnosis or detection, as described above, in virtually any immunological assay systems, of which immuno-fluorescence assays, radioimmunoassays, and enzyme-linked immunosorbent assays are examples only. Furthermore, the monoclonal antibodies of this invention can be used in a competitive binding or inhibition assay to measure other antibodies, either monoclonal or polyclonal, reactive with endotoxin core. Consequently, any assay system which employs monoclonal antibodies reactive with endotoxin core is embraced by this invention.

The monoclonal antibodies of this invention are reagents that may be used for the immunoprophylaxis or -therapy of Gram-negative infections, or their consequences, including septic shock. These clinical applications of the monoclonal antibodies of the invention are supported by their specificity for endotoxin core, their cross-reactivity with most Gram-negative bacteria, their ability to neutralize the biological activity of endotoxin, their cross-protective efficacy in experimental Gram-negative infections, and their producability in virtually limitless supply, thus overcoming a major shortcoming of polyclonal antibodies.

A composition in accordance with the present invention contains a concentration of the antibody effective in preventing or treating (i.e., ameliorating) infections caused by endotoxin-bearing microorganisms, or the consequences of such infections, including septic shock. The antibodies can be packaged and sold in freeze-dried or other acceptable form, and/or mixed with a therapeutically acceptable carrier, such as a balanced aqueous salt solution.

An immunoprophylactic or -therapeutic method in accordance with this invention entails the administration of the monoclonal antibodies of the invention by injection or infusion prior to (prophylaxis) or following (therapy) the onset of an infection caused by a pathogenic, endotoxin-bearing microorganism. The amount of antibody required to prevent or treat such an infection or its consequences depends upon such factors as the type and severity of the infection, the size and weight of the infected patient, and the effectiveness of other concomitantly employed modes of prophylaxis or therapy.

The monoclonal antibodies of this invention are useful reagents for research related to the structure and function of bacterial endotoxins. Their exquisite specificity allows them to be used for immunochemical and structure-activity analyses of endotoxin, and makes them more useful in these applications than less specific, conventional polyclonal antib.dioes. Moreover, the demonstrated cross-reactivity of the monoclonal antibodies of this invention with endotoxins from diverse bacteria confers upon them great versatility as investigational reagents.

A composition in accordance with the present invention useful as an investigational reagent contains an amount of antibody effective in providing information upon mixture with endotoxin and subsequent analysis. Determination of the amount of antibody necessary to accomplish a particular research goal depends upon the specific type of investigation involved, and is readily within the skill of one carrying out such research.

Likewise, a research method in accordance with this invention involves mixing the antibodies of the invention with endotoxin in such a way as to identify specific immuno-determinants and their biological or biochemical properties. The concentration of antibody used and the exact experimental format of such investigations depends on the type of research involved and can be readily determined by one skilled in doing such research.

The monoclonal antibodies of this invention are reagents that can be used for the isolation and purification of endotoxin contained in complex mixtures, and for the neutralization and/or removal of endotoxins from solutions which contain them. The novel attributes of monoclonal antibodies reactive with endotoxin core which make them particularly useful for these applications are their great specificity, compared with polyclonal antibodies, and their availability in virtually limitless quantities, which permits their use on a large, industrial or commercial scale.

A composition in accordance with the invention useful in purifying or removing endotoxin from complex mixtures contains an amount of antibody, contained in an appropriate solution or coupled to an appropriate matrix, to permit specific binding of endotoxin.

An immunological method in accordance with this invention effective in purifying or removing endotoxin from complex mixtures entails coupling antibodies of the invention to a suitable matrix (such as cyanogen bromide-activated Sepharose 4B, available from Pharmacia Fine Chemicals, Piscataway, N.J.). A complex mixture containing endotoxin can then be passed over a chromatographic column consisting of the monoclonal antibody coupled to the matrix. As a consequence of this procedure, endotoxin contained in the original mixture, or present as a contaminant in a solution, is specifically bound to the monoclonal antibody, which, in turn, is immobilized on the solid matrix. Everything contained in the complex mixture or contaminated solution, except the endotoxin itself, may be readily removed from the solid matrix by washing, and thus separated from the endotoxin which remains tightly bound. Finally, if one wishes to recover the bound endotoxin, now isolated on the solid matrix, various physical-chemical procedures (e.g., utilizing low pH, high ionic strength, or chaotropic ions such as thiocyanate) may be employed to release the endotoxin from the anti-endotoxin antibody. Endotoxin thus released will have been effectively separated from other components of the complex mixture in which it was originally contained, and it will now be highly purified as a consequence of this "affinity purification" or "immunoabsorption" procedure, utilizing the monoclonal antibodies of the invention.

Other embodiments and uses of the invention will be apparent to those skilled in the art from consideration of the specification and practice of the invention disclosed herein. It is intended that the specification and examples be considered as exemplary only, with the true scope and spirit of the claim being indicated by the following claims.

We claim:

1. A monoclonal antibody which binds to antigenic determinants in the endoxtoxin core of different genera of gram negative bacteria, said core consisting essentially of the lipid A and core oligosaccharide regions, and not the 0-side chain region of bacterial lipopolysaccharide, wherein said antibody:

a) binds to endotoxin core from at least one species of gram negative bacteria from each of the genera of Escherichia, Salmonella and Pseudomonas; and, b) is effective in treating clinical manifestations of infection in a mammalian host caused by gram negative bacteria when a therapeutically effective amount of said antibody is administered to the mammalian host.

2. A monoclonal antibody of claim 1 wherein said mammalian host is a human host.

3. A monoclonal antibody which binds to antigenic determinants in the endotoxin core of different genera of gram negative bacteria, said core consisting essentially of the lipid A and core oligosaccharide regions, and not the O-side chain region of bacterial lipopolysaccharide, wherein said antibody:
   a) binds to endotoxin core from at least one species of gram negative bacteria from each of the genera of Escherichia, Salmonella and Pseudomonas;
   b) is effective in treating clinical manifestations of infection in a mammalian host caused by gram negative bacteria when a therapeutically effective amount of said antibody is administered to the mammalian host; and,
   c) inhibits at least one biological response induced in mammalian cells by purified endotoxin in an in vitro assay.

4. A monoclonal antibody of claim 3 wherein said mammalian host is a human host.

5. A monoclonal antibody of claim 4 which inhibits endotoxin-induced mitogenesis in an in vitro assay with endotoxin-responsive B lymphccytes.

6. A pharmaceutical composition comprising a monoclonal antibody and a pharmaceutically acceptable carrier, said antibody being one which binds to antigenic determinants in the endotoxin core of different genera of gram negative bacteria, said core consisting essentially of the lipid A and core oligosaccharide regions, and not the O-side chain region of bacterial lipopolysaccharide, wherein said antibody:
   a) binds to endotoxin core from at least one species of gram negative bacteria from each of the genera of Escherichia, Salmonella and Pseudomonas; and,
   b) is effective in treating clinical manifestations of infection in a mammalian host caused by gram negative bacteria when a therapeutically effective amount of said antibody is administered to the mammalian host.

7. A pharmaceutical composition of claim 6 wherein said mammalian host is a human host.

8. A pharmaceutical composition of claim 7 wherein said antibody inhibits at least one biological response induced in mammalian cells by purified endotoxin in an in vitro assay.

9. A pharmaceutical composition of claim 8 wherein said antibody inhibits endotoxin-induced mitrogenesis in an in vitro assay with endotoxin-responsive B lymphocytes.

10. A method of treating clinical manifestations of infection in a mammalian host caused by gram negative bacteria by administering to said host a pharmaceutical composition comprising a therapeutically effective amount of monoclonal antibody in a pharmaceutically acceptable carrier, said monoclonal antibody binding to antigenic determinants in the endotoxin core of different genera of gram negative bacteria, wherein said core consists essentially of the lipid A and core oligosaccharide regions, and not the O-side chain region of bacterial lipopolysaccharide, wherein said antibody;
   (a) binds to endotoxin core from at least one species of gram negative bacteria from each of the genera of Escherichia, Salmonella and Pseudomonas; and,
   (b) is effeective in treating clinical manifestations of infection in a mammalian host caused by gram negative bacteria when a therapeutically effective amount of said antibody is administered to the mammalian host.

11. A method of treating of claim 10 wherein said mammalian host is a human host.

12. A method of treating of claim 11 wherein said monoclonal antibody inhibits at least one biological response induced in mammalian cells by purified endotoxin in an in vitro assay.

13. A method of treating of claim 12 wherein said monoclonal antibody inhibits endotoxin-induced mitogenesis in an in vitro assay with endotoxin-responsive B lymphocytes.

14. A method of inhibiting clinical manifestations of infection in a mammalian host caused by gram negative bacteria by administering to said host a pharmaceutical composition comprising a prophylactically effective amount of monoclonal antibody in a pharmaceutically acceptable carrier, said monoclonal antibody binding to antigenic determinants in the endotoxin core of different genera of gram negative bacteria, wherein said core consists essentially of the lipid A and core oligosaccharide regions, and not the O-side chain region of bacterial lipopolysaccharide, wherein said antibody:
   (a) binds to endotoxin core from at least one species of gram negative bacteria from each of the genera of Escherichia, Salmonella and Pseudomonas; and,
   (b) is effective in treating clinical manifestations of infection in a mammalian host caused by gram negative bacteria when a therapeutically effective amount of said antibody is administered to the mammalian host.

15. A method of inhibiting of claim 14 wherein said mammalian host is a human host.

16. A method of inhibiting of claim 15 wherein said monoclonal antibody inhibits at least one biological response induced in mammalian cells by purified endotoxin in an in vitro assay.

17. A method of inhibiting of claim 16 wherein said monoclonal antibody inhibits endotoxin-induced mitogenesis in an in vitro assay with endotoxin-responsive B lymphocytes.

* * * * *